United States Patent [19]
Eagles et al.

[11] Patent Number: 6,048,542
[45] Date of Patent: Apr. 11, 2000

[54] INHIBITING GROWTH OF MICROORGANISMS IN WATER-BASED PESTICIDE SUSPENSIONS

[75] Inventors: Karen L. Eagles, Raymore; Donald W. Edson, Lathrop, both of Mo.

[73] Assignee: Bayer Corporation, Pittsburgh, Pa.

[21] Appl. No.: 09/264,202

[22] Filed: Mar. 8, 1999

[51] Int. Cl.[7] .......................... A01N 25/00; A01N 43/64; A01N 43/40

[52] U.S. Cl. .......................... 424/405; 514/242; 514/341; 514/383

[58] Field of Search .............................. 504/116; 424/405; 514/242, 341, 383

[56] References Cited

U.S. PATENT DOCUMENTS 5,104,873  4/1992  Nowak et al. .......................... 514/245
5,283,231  2/1994  Morgan et al. .......................... 504/148
5,672,617  9/1997  Wachtler et al. ........................ 514/407

*Primary Examiner*—S. Mark Clardy
*Assistant Examiner*—Alton Pryor
*Attorney, Agent, or Firm*—Joseph C. Gil; Carol Marmo

[57] ABSTRACT

The present invention provides a composition for inhibiting the growth of microorganisms in water-based pesticide suspensions. In accordance with this invention, the composition comprises from about 0.01% to about 60% by weight of a pesticide; from about 0% to about 20% by weight of a surfactant; from about 0% to about 20% by weight of an antifreeze agent; from about 0% to about 5% by weight of a viscosity builder; from about 0.5% to about 2% by weight of acetic acid; and from about 10% to about 99.49% by weight of water. In a preferred embodiment of the invention, the acetic acid has a pH of from about 3 to about 5.

8 Claims, No Drawings

INHIBITING GROWTH OF MICROORGANISMS IN WATER-BASED PESTICIDE SUSPENSIONS

TECHNICAL FIELD OF THE INVENTION

The present invention relates to a composition for inhibiting or eliminating the growth of microorganisms in water-based pesticide suspensions. More particularly, the composition of the present invention comprises a pesticide, a surfactant, an antifreeze agent, a viscosity builder, acetic acid, and water. Acetic acid is present in an amount of from about 0.5% to about 2% by weight of the total pesticide suspension. The pH of the acetic acid is from about 3 to about 5.

BACKGROUND OF THE INVENTION

A pesticide suspension is a homogeneous mixture of small solid particles of pesticide suspended in a liquid medium. The growth of microorganisms in the pesticide suspension can cause a solid precipitate to form and therefore, a loss of homogeneity in the mixture. Formation of the precipitate and the loss of homogeneity can result in product failure due to non-uniform applications of the pesticide, and plugging of strainers and nozzles used with application equipment.

A practice developed in the art of combining or formulating the pesticide compounds with a preservative to reduce or eliminate the growth of microorganisms in pesticide suspensions. U.S. Pat. No. 5,283,231 describes formaldehyde, sodium benzoate, glutaraldehyde, and pentachlorophenol, as effective preservatives to prevent microbial spoiling in low-melting dinitroaniline pesticide suspensions.

Not all preservatives are effective against all types of microorganisms, in all pesticide suspensions. Thus, there is a need in the art to determine specific preservatives that are effective in a particular flowable aqueous pesticide composition (i) to reduce or eliminate the growth of microorganisms, (ii) while being easy to handle during preparation and use, and (iii) maintaining an excellent shelf-life even during extended storage.

SUMMARY OF THE INVENTION

It is an object of the present invention to provide a composition for inhibiting or eliminating the growth of microorganisms in water-based pesticide suspensions. This and other objects which will be apparent to those skilled in the art are accomplished by the addition of acetic acid to the water-based pesticide formulation. The composition of the water-based pesticide formulation includes from about 0.01% to about 60% by weight of a pesticide; from about 0% to about 20% by weight of a surfactant; from about 0% to about 20% by weight of an antifreeze agent; from about 0% to about 5% of a viscosity builder, and from about 10% to about 99.49% of water. Acetic acid is added to the water-based pesticide formulation in an amount of from about 0.5% to about 2% by weight of the formulation. The pH of the acetic acid is from about 3 to about 5.

DETAILED DESCRIPTION OF THE PREFERRED EMBODIMENTS OF THE INVENTION

The composition of the pesticide suspension of the present invention comprises a combination of a water-based pesticide formulation and acetic acid. The pesticide formulation includes a pesticide; a surfactant; a thickener; an antifreeze agent; and water. The pesticide is selected from the group consisting of an insecticide, a fungicide, and a herbicide. Preferably, the insecticide is imidacloprid, the fungicide is tebuconazole, and the herbicide is metribuzin. The pesticide is present in an amount such that it comprises from about 0.01% to about 60% by weight of the entire pesticide suspension.

Surfactants serve to reduce the surface tension at the water-solid interface and, therefore, increase the tendency of the water to contact the complete surface of the active ingredient particles. Suitable surfactants include wetting agents and dispersing agents. Further, both anionic and nonionic surfactants are useful. Examples of anionic surfactants include arylalkyl sulfonates and alkyl naphthalene sulfonates. Nonionic surfactants include arylalkyl polyether alcohols, polyalkylene oxide block copolymers polyalkylene oxide block copolymer monohydric alcohols and polyalkylene oxide block copolymer alkyl phenols. Preferred surfactants include naphthalene formaldehyde condensates, naphthalene sulfonates, alkyl naphthalene sulfonates, lignosulfonates, ethylene oxide and propylene oxide block copolymers, alkyl alcohol ethoxylates, alkyl phenol ethoxylates, sodium dodecylbenzene sulfonates, tristyryl phenol ethoxylates, alkyl ethylene oxide and propylene oxide block copolymers, polyacrylates, and phosphate esters. The amount of surfactant in the pesticide formulation is such that it comprises from about 0% to about 20% by weight, of the entire pesticide suspension.

A viscosity builder is generally a water soluble or water dispersible anionic colloid possessing shear thinning properties, low sensitivity to temperature, good stability in both acidic and basic media, and compatibility with most inorganic materials. Suitable viscosity builders include thickening agents. Examples of viscosity builders include polysacharide gums such as xanthan gum, guar gum, gum arabic; organically modified montmorillonite clays, attapulgite clays, carboxy-vinyl copolymers, and cellulose ethers. Preferred viscosity builders include xanthan gum, magnesium aluminum silicates, plant extract thickeners, and cellulose derivative thickeners. The viscosity builder is present in an amount such that it comprises from about 0% to about 5% by weight of the entire pesticide suspension.

An antifreeze agent is a freeze point depressant. Examples of antifreeze agents include relatively low molecular weight aliphatic alcohols. Preferred anti-freeze agents include glycols, glycerine, and urea. The amount of antifreeze agent in the pesticide formulation is such that it comprises from about 0% to about 20% by weight, of the entire pesticide suspension.

The acetic acid in the composition serves as a preservative which is used to reduce or eliminate the growth of microorganisms in the mixture. The acetic acid is present in an amount such that it comprises from about 0.5% to about 2% by weight of the entire pesticide suspension, and preferably from about 0.6% to about 1% by weight. Further, in a preferred embodiment, the acetic acid has a pH of from about 3 to about 5.

The composition of the pesticide suspension also includes from about 10% to about 99.49% by weight of water.

The composition of the pesticide suspension of the present invention is generally as follows.

| Ingredient | Weight % |
| --- | --- |
| Pesticide | 0.01%–60% |
| Surfactant | 0%–20% |
| Viscosity Builder | 0%–5% |

-continued

| Ingredient | Weight % |
|---|---|
| Antifreeze Agent | 0%–20% |
| Acetic Acid | 0.5%–2% |
| Water | 10%–99.49% |

Having thus described our invention, the following examples are given as being illustrative thereof; and they are in no way meant to be limiting of the specification and the claims. All weights and percentages given are parts by weight or percentages by weight, unless otherwise indicated.

EXAMPLES

Example 1

A study was conducted to demonstrate the effectiveness of adding from about 0.0% to about 1% by weight of acetic acid to inhibit or eliminate the growth of microorganisms in a water-based suspension concentrate (SC) containing 2 pounds per gallon of insecticide (ADMIRE 2F). The insecticide formulation was blended together and homogenized by means of a high-shear mixer. The composition of the insecticide formulation included about 21% by weight of a finely milled solid insecticide, about 4% by weight of a surfactant, about 10% by weight of an anti-freeze agent, about 0.18% by weight of a viscosity builder, about 64% by weight of water, and levels of acetic acid ranging from 0.0% to 1.0% as shown in Table 1 below. The acetic acid had a pH in the range of 3 to 5. The samples were then inoculated with bacteria species that were specific to the production site, and were evaluated over a 72 hour period at a temperature of about 30° C.

TABLE 1

| Acetic Acid | Bacteria Present/ml | | | | | |
|---|---|---|---|---|---|---|
| | Time (hrs): | | | | | |
| (wt. %) | 0 | 12 | 24 | 36 | 48 | 72 |
| 0.0 | 1E06 | 1.5E06 | 2E06 | 2.5E06 | 2.5E06 | 3E06 |
| 0.2 | 1E06 | 1.5E06 | 2E06 | 2.5E06 | 2.5E06 | 3E06 |
| 0.4 | 1E06 | 1E06 | 1E06 | 1.5E06 | 1.5E06 | 2E06 |
| 0.6 | 1E06 | 0 | 0 | 0 | 0 | 0 |
| 0.8 | 1E06 | 0 | 0 | 0 | 0 | 0 |
| 1.0 | 1E06 | 0 | 0 | 0 | 0 | 0 |

Example 2

A study was conducted to demonstrate the effectiveness of 0.0% to 1% by weight of acetic acid in inhibiting or eliminating the growth of microorganisms in a water-based suspension concentrate (SC) containing 1.6 pounds per gallon of insecticide (PROVADO 1.6F). The insecticide formulation was blended together and homogenized by means of a high-shear mixer. The composition of the insecticide formulation included about 17% by weight of a finely milled solid insecticide, about 4% by weight of a surfactant, about 10% by weight of an anti-freeze agent, about 0.25% by weight of a viscosity builder, about 68% by weight of water, and levels of acetic acid ranging from 0.0% to 1.0% as shown in Table 2 below. The pH of the acetic acid was in the range of 3 to 5. The samples were then inoculated with bacteria species that were specific to the production site, and were evaluated over a 72 hour period at a temperature of about 30° C.

TABLE 2

| Acetic Acid | Bacteria Present/ml | | | | | |
|---|---|---|---|---|---|---|
| | Time (hrs): | | | | | |
| (wt. %) | 0 | 12 | 24 | 36 | 48 | 72 |
| 0.0 | 1E06 | 1.5E06 | 2E06 | 2.5E06 | 2.5E06 | 3E06 |
| 0.2 | 1E06 | 1.5E06 | 2E06 | 2.5E06 | 2.5E06 | 3E06 |
| 0.4 | 1E06 | 1E06 | 1E06 | 1.5E06 | 1.5E06 | 2E06 |
| 0.6 | 1E06 | 0 | 0 | 0 | 0 | 0 |
| 0.8 | 1E06 | 0 | 0 | 0 | 0 | 0 |
| 1.0 | 1E06 | 0 | 0 | 0 | 0 | 0 |

The results shown in Tables 1 and 2 demonstrate that the addition of from about 0.6% by weight to about 1% by weight of acetic acid to the water-based pesticide suspension was effective to eliminate the growth of microorganisms throughout the 72 hour testing period.

Although the invention has been described in detail in the foregoing for the purpose of illustration, it is to be understood that such detail is solely for that purpose and that variations can be made therein by those skilled in the art without departing from the spirit and scope of the invention except it may be limited by the claims.

What is claimed is:

1. A composition for inhibiting or eliminating the growth of microorganisms in water-based pesticide suspensions, comprising:
   a. a pesticide in an amount of from about 0.01% up to about 60% by weight;
   b. a surfactant that is present in an amount up to about 20% by weight;
   c. an antifreeze agent that is present in an amount up to about 20% by weight;
   d. a viscosity builder that is present in amount up to about 5% by weight;
   e. acetic acid in an amount of from about 0.5% up to about 2% by weight; and
   f. water in an amount of from about 10% up to about 99.49% by weight.

2. The composition of claim 1 wherein the acetic acid is present in an amount of from about 0.6% to about 1.0% by weight of the pesticide suspension.

3. The composition of claim 1 wherein the pesticide is selected from the group consisting of an insecticide, a herbicide, and a fungicide.

4. The composition of claim 2 wherein the insecticide is imidacloprid.

5. The composition of claim 1 wherein the surfactant is selected from the group consisting of naphthalene/formaldehyde condensates, naphthalene sulfonates, alkyl naphthalene sulfonates, lignosulfonates, ethylene oxide/propylene oxide block copolymers, alkyl alcohol ethoxylates, alkyl phenol ethoxylates, sodium dodecyl benzene sulfonates, tristyryl phenol ethoxylates, alkyl ethylene oxide/propylene oxide block copolymers, polyacrylates, and phosphate esters.

6. The composition of claim 1 wherein the antifreeze agent is selected from the group consisting of glycerine, glycols, and urea.

7. The composition of claim 1 wherein the viscosity builder is selected from the group consisting of xanthan gum, magnesium aluminum silicates, plant extract thickeners, and cellulose derivative thickeners.

8. The composition of claim 1 wherein the pH of the acetic acid is from about 3 to about 5.

* * * * *